(12) United States Patent
Tanaka et al.

(10) Patent No.: US 6,355,260 B1
(45) Date of Patent: Mar. 12, 2002

(54) INORGANIC COMPOUND-COATED PIGMENTS AND COSMETICS USING THE SAME

(75) Inventors: Hirokazu Tanaka; Takumi Miyazaki, both of Fukuoka (JP)

(73) Assignee: Catalysts & Chemicals Industries Co., Ltd., Kawasaki (JP)

( * ) Notice: Subject to any disclaimer, the term of this patent is extended or adjusted under 35 U.S.C. 154(b) by 0 days.

(21) Appl. No.: 09/319,176

(22) PCT Filed: Dec. 8, 1997

(86) PCT No.: PCT/JP97/04481

§ 371 Date: Jun. 3, 1999

§ 102(e) Date: Jun. 3, 1999

(87) PCT Pub. No.: WO98/26011

PCT Pub. Date: Jun. 18, 1998

(30) Foreign Application Priority Data

Dec. 10, 1996 (JP) .............................................. 8-346760

(51) Int. Cl.⁷ ................................................. A61K 7/02
(52) U.S. Cl. ........................ 424/401; 424/489; 424/490; 424/63; 424/64; 424/69

(58) Field of Search .................................. 424/489, 490, 424/69, 63, 64, 401

(56) References Cited

U.S. PATENT DOCUMENTS 5,607,504 A * 3/1997 Schmid et al. .............. 106/403

FOREIGN PATENT DOCUMENTS

| JP | 60-226805 | 11/1985 |
| JP | 7-257930 | 10/1995 |
| JP | 8-59238 | 3/1996 |
| JP | 8-209024 | 8/1996 |

* cited by examiner

*Primary Examiner*—Michael A. Williamson
(74) *Attorney, Agent, or Firm*—Kanesaka & Takeuchi

(57) ABSTRACT

White or colored pigments which do not suffer from color tone or hiding performances thereof even when the surface is moistened with water or oil, without spoiling coloring performance or hiding performance of the pigments themselves. These pigments are surface-coated with an inorganic compound having the refractive index of 1.8 or below. The inorganic compound is preferably silicon oxide, and the pigments are preferably inorganic pigments comprising titanium oxide, zinc oxide, or iron oxide. The cosmetics of the invention are blended the pigments therein.

8 Claims, 5 Drawing Sheets

INORGANIC COMPOUND-COATED PIGMENTS AND COSMETICS USING THE SAME

FIELD OF THE INVENTION

The present invention relates to pigments having the surface coated with a particular inorganic compound, and more specifically to white or colored pigments with improved capability for preventing change of the color caused when wet with water or oil and degradation in hiding performances thereof. Furthermore the present invention relates to cosmetics with the white or colored pigment blended therein.

BACKGROUND TECHNOLOGY

White pigments such as titanium oxide or zinc oxide and inorganic colored pigments such as Indian red, yellow iron oxide, black iron oxide, and ultramarine blue pigment, or organic pigments such as tar coloring matter generally change the colors to darker ones when wet with water or oil with the hiding performances degraded. This phenomenon occurs because a light reflectance or a scattering effect of the surface of pigments becomes lower.

By mixing the white or colored pigment as described above in cosmetics used for making-up, there are provided effects such as those of covering defects of human skin such as wrinkles or masculae or a coloring effect to make human skin look more attractive. However, as time goes by after the cosmetic is applied to human skin and a surface of pigments blended therein is wet with skin fats or sweat, a reflectance or scattering capability of the pigments becomes smaller with a color tone of the cosmetic film changing and also with the masking capability becoming lower, so that the capability of the cosmetics to cover human skin degrades.

There has been used a method of giving water repellency or oil repellency to pigments by treating with silicon-based or fluorine-based compounds to improve a stability in use for a long time of cosmetics. With this kind of cosmetics, the cosmetic effect can be preserved for a longer period of time to some extent by making it harder to be wet with skin fat or sweat, but the adequate stability in use for a long time has not be realized.

Further there is a method of preventing or delaying a pigment from getting wet by simultaneously mixing porous silica or the like in cosmetics so that skin fats or sweat secreted in association with passage of time is absorbed in the silica or the like, but the effect is not adequate at present.

Further in some of the cosmetics with the white or colored pigments blended therein, sometimes oil and fat, moistener, a surfactant, an organic thickener, an organic solvent or the like blended in cosmetics may be oxidized or decomposed, which in turn degrades the appearance or performance. Also in cosmetics with certain types of colored pigments blended therein, active oxygen is generated, and this active oxygen may promote aging of human skin onto which the cosmetics is applied.

DISCLOSURE OF THE INVENTION

It is an object of the present invention to provide white or colored pigments, which do not suffer from color tone or hiding performances thereof even when the surface is moistened with water or oil, without spoiling coloring performance or hiding performance of the pigments themselves.

Further it is another object of the present invention to provide cosmetics which can preserve the excellent effect for a long period of time and does not change the color tone by oxidizing or decomposing organic compounds blended therein nor lower its appearance and performances.

In the pigments according to the present invention, surfaces of the pigments are covered with an inorganic compound having the refractive index of 1. 8 or below.

The inorganic compound is preferably silicon oxide. The pigments are preferably inorganic pigments comprising titanium oxide, zinc oxide, or iron oxides In the cosmetics according to the present invention, the pigments are blended therein.

BRIEF DESCRIPTION OF THE INVENTION

BEST MODE FOR CARRYING OUT THE INVENTION

Figure 1:
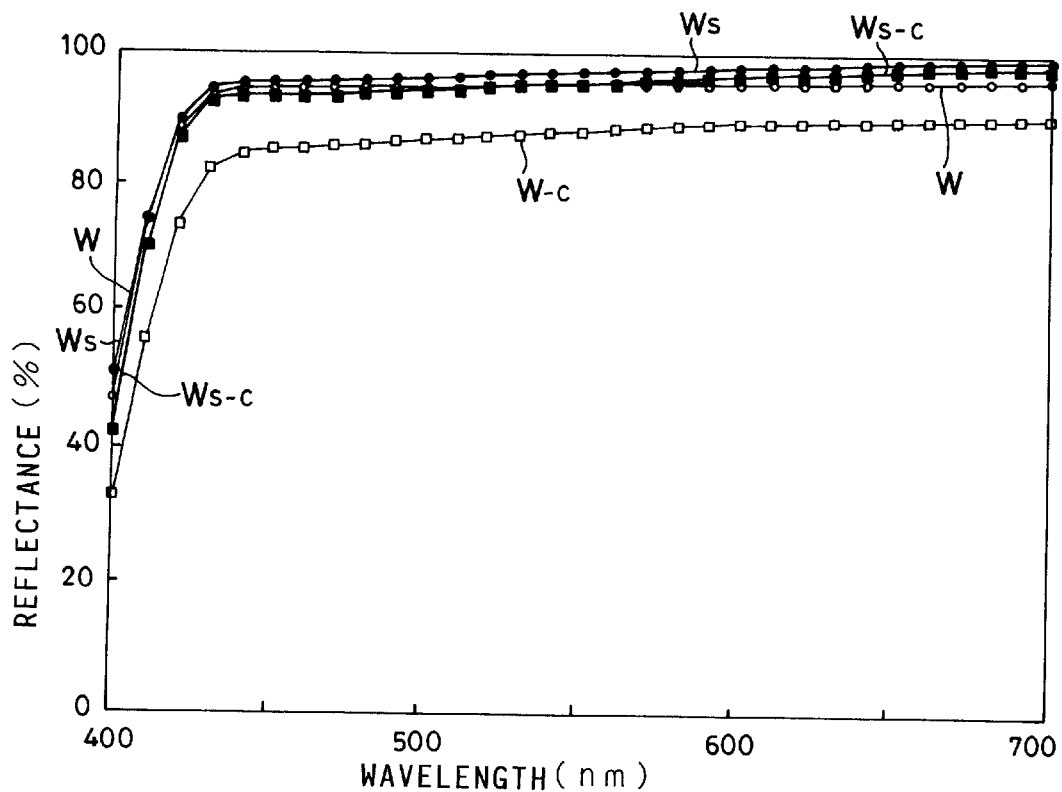
FIG. 1 is a graph showing a change in the reflectance when white pigments (W, Ws) are moistened with CTG.

Detailed description is made hereinafter for preferable embodiments of the present invention.

Generally a reflectance and a scattering coefficient of substance are decided by a difference and a ratio between the refractive index of the substance and that of medium present around the substance, and when the difference and the ratio become smaller, the reflectance and the scattering coefficient become lower.

The expression (1) below is that developed by Fresnel for a reflectance R of a substance. The expression (2) is that for calculating a light scattering coefficient S in which the expression developed by Rayleigh for a scattering coefficient of light is applied:

$$R=[(n_p-n_b)/(n_p+n_b)]^2 \qquad (1)$$

wherein $n_p$ is a refractive index of particles, and $n_b$ is a refractive index of medium.

$$S=\alpha[(m^2+1)/(m^2+1)]^2 \qquad (2)$$

wherein m is $n_p/n_b$ and $\alpha$ is a coefficient.

For the reasons as described above, reflectances R and scattering coefficients S of titanium oxide as white pigments (with the refractive index of 2.72), Indian red (with the refractive index of 2.78), yellow iron oxide (with the refractive index of 2.00) or the like are generally decided by a difference and a ratio between a refractive index of each of the substances and that of air as a medium.

When a surface of the pigment is moistened, for instance, with water, the medium changes from air with the refractive index of 1.00 to water with the refractive index of 1.33, so that the reflectance R and the scattering coefficient S before moistened with water are different from those after moistened with water.

On the other hand, a refractive index of silica which is an inorganic compound is 1.47, and as the refractive index is smaller than that of the pigments described above, the difference and the ratio between the refractive index of the substance before moistened with water and that after moistened with water is smaller as compared to that of the pigments. Namely a change in the reflectance R and the scattering coefficient S is smaller.

An object of the present invention is to provide pigments which suppress the change of the reflectance and the scattering coefficient even when moistened with, for instance, water by covering a surface of the white or colored pigment generally having a large refractive index with a substance having a low refractive index which is close to that of water or oil.

Ordinary inorganic pigments or organic pigments are used in the present invention. The inorganic pigments, which can be used according to the present invention, include such as titanium oxide, zinc oxide, zirconium oxide, cerium oxide, Indian red, yellow iron oxide, black iron oxide, ultramarine blue, dark blue, barium sulfate, titanated mica, mica, sericite, talc, bentonite, kaolin, and mixed pigments having a color of human skin comprising titanium oxide and iron oxide. Organic pigments available according to the present invention include Red No. 202 (lithol rubine BCA), Red No. 203 (lake red C), Red No. 204 (lake red CBA), Red No. 205 (lithol red), Red No. 207 (lithol red BA), Orange No. 203 (permanent orange), Orange No. 204 (benzidine orange G), Yellow No. 205 (benzidine yellow G), Blue No. 201 (indigo), Blue No. 204 (carbanthrene blue).

These pigments are generally white or colored particles, and the average diameter of the particles is preferably in a range from 0.1 to 1 µm. There is no specific limitation concerning a form of the particles, and the particles may have any forms including a sphere, a rod, a needle, a plate and a flake.

As an inorganic compound having a low refractive index used for covering a surface of the pigment particle, an inorganic oxide having a refractive index in a range from 1.8 to 1.2, and preferably in range from 1.7 to 1.4 should be used, and the inorganic compounds include silica (with the refractive index of 1.47), alumina (with the refractive index of 1.7), and phosphorus oxide (with the refractive index of 1.7).

As for a method of covering the surfaces of pigment particles with the inorganic compounds as described above, there is no specific limitation on the condition that the inorganic compounds can homogeneously be spread over the surfaces of the pigment particles. For instance, there can be enumerated the method in which a silica coating film is formed by adding a silicic acid solution in a dispersion of the pigment particles for having the silicic acid polymer deposited on the surfaces of the pigment particles. Also the method can be used in which a hydrolytic organic silicon compound such as tetraethoxysilane is added in a dispersion of the pigment particles so that the organic silicon compound is hydrolyzed to form a silica coating film on the surfaces of the pigment particles.

An alumina coating film can be formed on the surfaces of pigment particles by adding an organic aluminium compound such as aluminium tetraalkoxide in a dispersion of pigment particles for hydrolysis or by adding a sulfate, a hydrochloride, a nitrate, or organic salts of aluminium.

A relative quantity of an inorganic compound used for coating against 100 weight parts of pigments is in a range from 1 to 40 weight parts, and preferably in a range from 5 to 30 weight parts. If the rate is less than one weight part, the effect can not be expected, and when the rate is more than 40 weight parts, the hiding performances become lower, or the coloring capability becomes lower.

Next, description is made for the cosmetics according to the present invention. The cosmetics according to the present invention contain the pigments according to the present invention as described above, but the cosmetics never oxidize nor decompose an organic compound blended therein such as oil with a volume of active oxygen generated rather small, and in addition direct contact of the pigments with human skin is suppressed, so that aging of skin can be prevented. Further a color tone of the cosmetics does not change with the appearance and performances not being lowered.

A blending rate of the pigments in the cosmetics according to the present invention is preferably in a range from 1 to 80 weight %. When the rate is less than 1 weight %, the blending effect is not obtained at all, and if the rate surpasses 80 weight %, the hiding performances become too strong, which hinders the natural effect provided by the cosmetics.

It should be noted that, when the coated pigments according to the present invention are blended in cosmetics, the surfaces of the pigments may be treated with a silicone or a fluorine compound.

The cosmetics according to the present invention contain various types of components blended in the ordinary cosmetics, namely at least one or more of higher aliphatic alcohols; higher fatty acids; oils such as ester oil, paraffin oil, and wax; alcohols such as ethyl alcohol, propylene glycol, sorbitol, and glycerin; moistners such as mucopolysaccharide, collagens, PCA salts, lactate; various types of surfactants such as nonion-based, cation-based, anion-based, or amphoric surfactants; thickners such as gum arabic, xanthan gum, polyvinylpyrrolidone, ethyl cellulose, carboxymethyl cellulose, carboxyvinyl polymer, denatured or not-denatured clay minerals; solvents such as ethyl acetate, acetone, toluene; inorganic pigments/dyes; organic pigments/dyes; antioxydants such as BHT, tocopherol; water; drugs; ultraviolet absorbent; pH buffers; chelating agents; preservatives; and perfumes. Also at least one or more of inorganic fillers such as silica, talc, kaolin, mica; extender pigments, and various types of organic resin may be contained therein.

The cosmetics according to the present invention may be manufactured by using any conventional technology, and is used in various forms including powder, cake, pencil, stick, liquid, and cream, and more specifically foundations, cream, emulsions, eye-shadow, base for cosmetics, nail enamel, eye liner, mascara, lipsticks, pack, cosmetic water, shampoo, rinse, hair colors are included in the cosmetics according to the present invention.

DETAILED DESCRIPTION OF THE EMBODIMENTS

Detailed description is made hereinafter for embodiments of the present invention, and the embodiments are provided only for explaining the present invention. As pigments for the present invention, inorganic compounds other than those used in the embodiments described below, such as alumina or phosphorus oxide may be used. So the present invention is not limited to the embodiments described below. A scope of the present invention is defined by the Claims, and is not restricted by descriptions in the specification. Variants and modifications within equivalent scopes of the Claims are within a scope of the present invention.

Embodiment 1

90 g white pigments (W) made of titanium oxide and having an average particle diameter of 250 nm was mixed in one litter of ethanol to prepare a dispersion. This dispersion was heated to 45° C. and 28% aqueous annomia was added to adjust pH to 9.5 or more, and then tetraethoxysilane with the weight equivalent to 10 g of $SiO_2$ and 110 g of 28% aqueous ammonia was added to the dispersion while preserving the conditions described above. After addition of the compounds described above, the dispersion was further agitated for additional two hours, and then filtered, washed, and dried under the temperature of 110° C., and further sintered under the temperature of 600° C., and silica-coated titanium oxide white pigments (Ws) were obtained. The white pigments were observed with an electronic microscope, and it was found that the particles were not aggregated and the particle shapes and diameters before and after coating with silica were substantially homogeneous.

Figure 2:
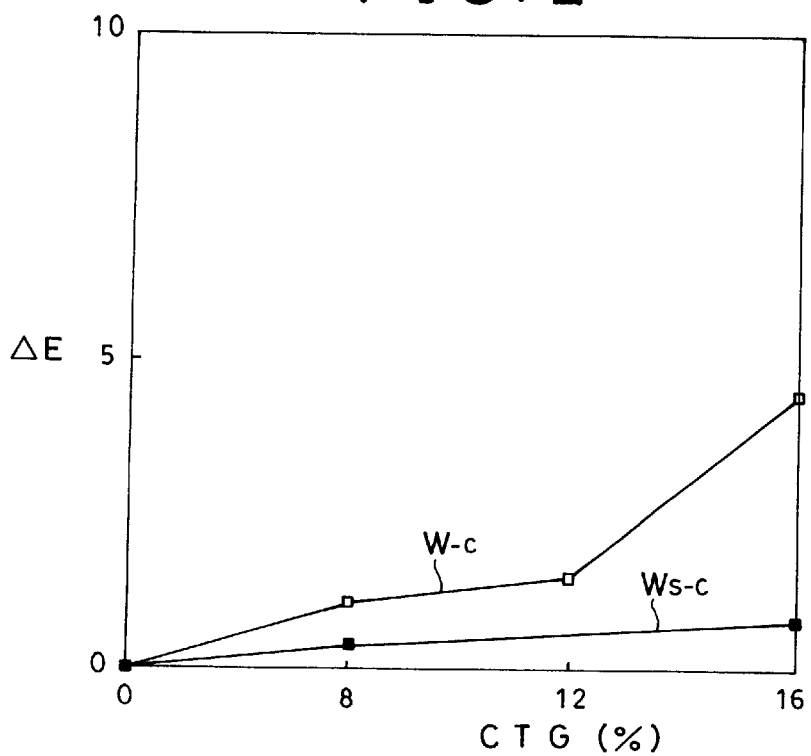
FIG. 2 is a graph showing a color difference of the white pigments (W, Ws) when the pigments are moistened with CTG.

Change of a color tone when the resultant silica-coated white pigments were moistened with water and by oil was assessed in the following way. At first, silica-coated white pigments (Ws) and titanium oxide white pigments non-coated with silica (W) were mixed with caprylic triglyceride (sometimes described as CTG hereinafter), which is a main component of sebum, at the pigments vs CTG ratio of 84/16 (weight ratio) to prepare pigment samples (Ws-c) and (W-c) moistened with CTG respectively. Reflectances of these samples were measured with a colorimeter (manufactured by Minolta, CM-2002), and a result of measurement is shown in FIG. 1. In a case where a mixing ratio of pigments vs CTG was changed, changes in a color difference (ΔE) between colors when CTG was mixed in the silica-coated white pigments (Ws-c) as well as in titanium oxide white pigments non-coated with silica (W-c) and those when CTG was not mixed therein were measured with the same colorimeter and a result of measurement is shown in FIG. 2.

Figure 3:
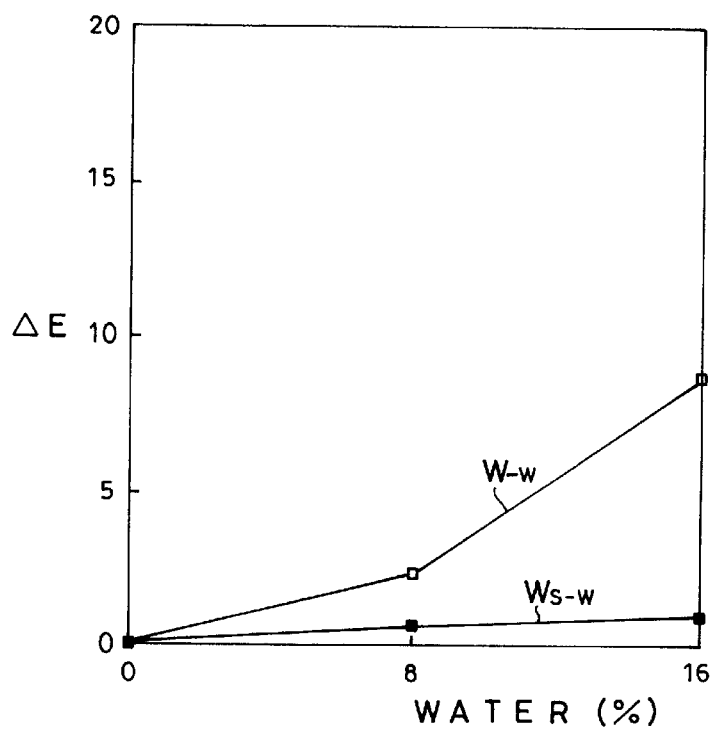
FIG. 3 is a graph showing a color difference of the white pigments (W, Ws) when the pigments are moistened with water.

Next, when pigments and water were mixed and the mixing ratio was changed, changes in color differences (ΔE) of white pigments coated with silica (Ws-w) and of white pigments non-coated with silica (W-w) were measured similarly, and a result of the measurement is shown in FIG. 3.

Measured values for color differences (ΔE) in samples when the mixing ratio of pigments/CTG was 84/16 (weight ratio) and when the mixing ratio of pigments/water was 84/16 (weight ratio) and decrease rate (%) in color differences of the white pigments coated with silica against white pigments non-coated with silica (Ws) are shown in Table 1.

It should be noted that the term of color difference(ΔE) as defined herein quantitatively shows a visual difference colors and is obtained by using Hunter's color difference formula as defined in 6.3.2 JIS Z 8730 (Method for Specification Color Difference). The color difference formula is as shown below:

$$\Delta E=[(\Delta L)^2+(\Delta a)^2+(\Delta b)^2]^{1/2}$$

wherein ΔL, Δa and Δb are differences of brightness index L, and chromaticness indexes a and b between two surface colors in Hunter's color difference formula.

TABLE 1

|  | Color difference (ΔE) | |
|---|---|---|
|  | CTG 16 wt % | Water 16 wt % |
| Non-coated white pigments (W): | 4.5 | 8.8 |
| Silica-coated white pigments (Ws): | 0.73 | 0.95 |
| Decrease rate (%) of ΔE: | 84 | 89 |

In FIG. 1, before CTG was mixed, a spectral reflectance of the white pigments coated with silica (Ws) is substantially not different from that of the white pigments non-coated with silica (W), but after CTG was mixed therein, comparison of the spectral reflectances shows that a decrease rate in the white pigments coated with silica (Ws) is smaller.

Also it can be observed that, also for the color difference (ΔE), change in the white pigments coated with silica (Ws-C), (Ws-w) is smaller, which clearly indicates that change in a color tone of the white pigments coated with silica was suppressed.

Embodiment 2

Indian red pigments coated with silica (Rs) was obtained by the same method as that described above excluding only the point that Indian red pigments (R) made from needle-shaped particles each having an average length of 500 nm and an average diameter of 100 nm was used in place of the titanium oxide used in Embodiment 1. Observation of the red pigments with an electronic microscope showed that the particles had not be aggregated and particles shapes and diameters before and after coating with silica were substantially identical.

Figure 4:
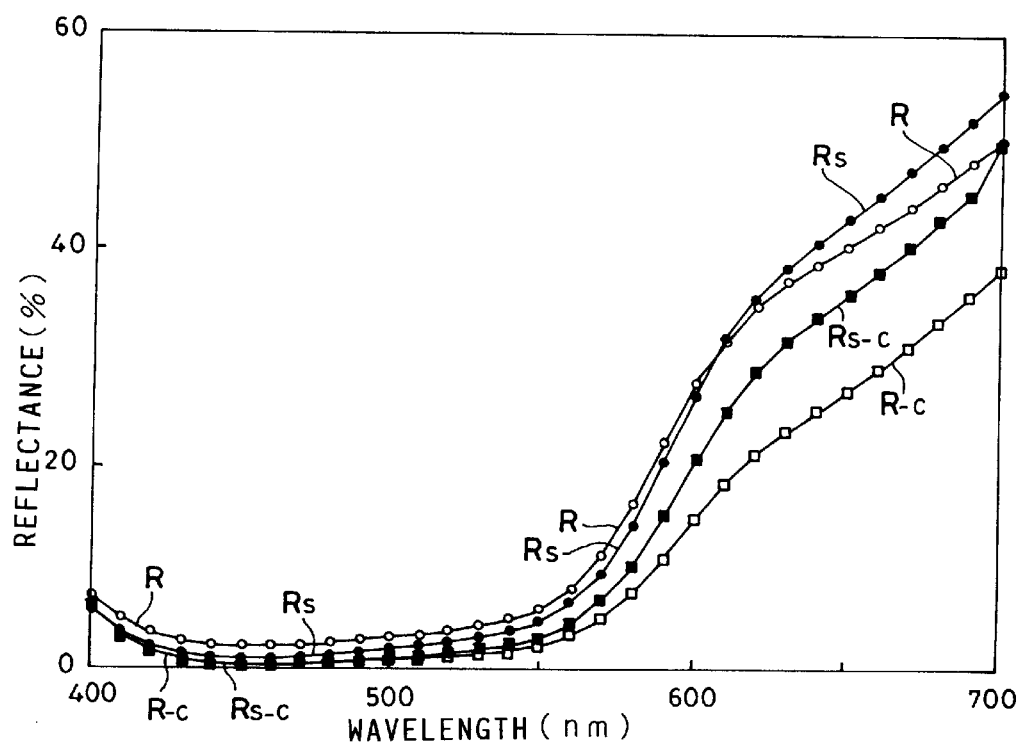
FIG. 4 is a graph showing a change in the reflectance when red pigments (R,Rs) are moistened with CTG.
Figure 5:
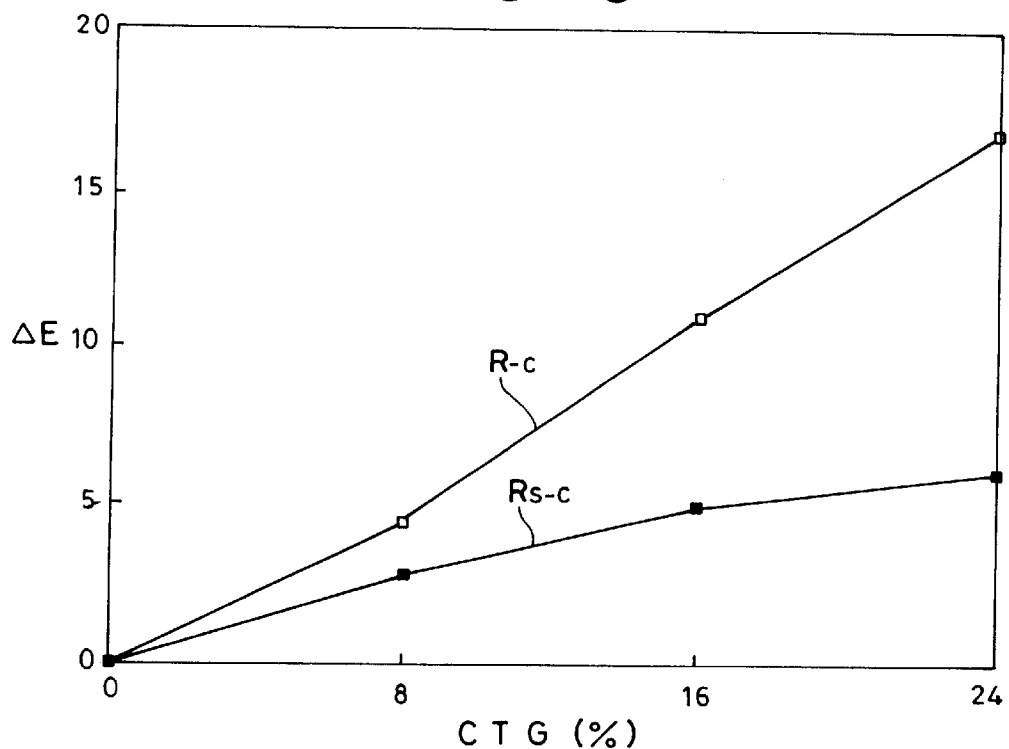
FIG. 5 is a graph showing a color difference of the red pigments (R, Rs) when the pigments are moistened with CTG.
Figure 6:
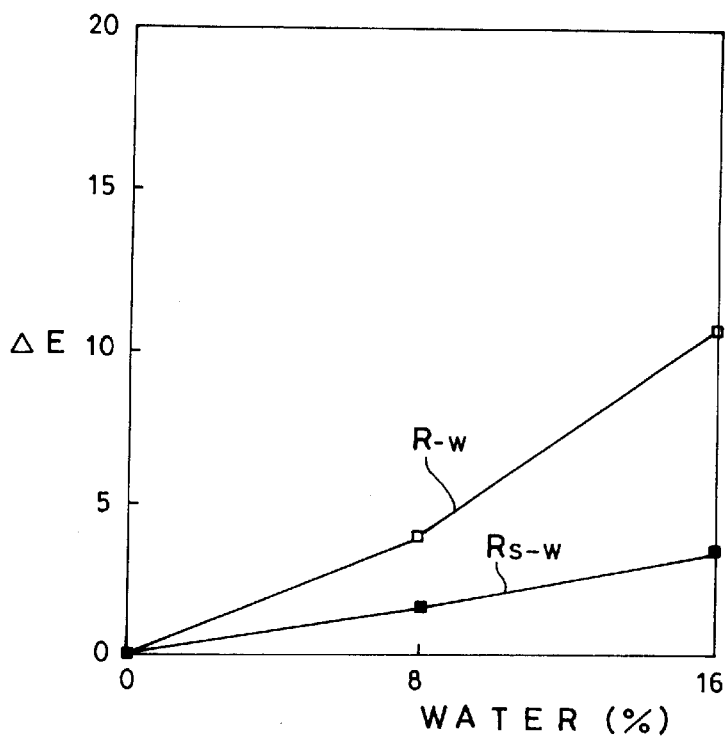
FIG. 6 is a graph showing a color difference of the red pigments (R, Rs) when the pigments are moistened with water.

Changes of a color tone for the resultant red pigments coated with silica (Rs) and red pigments non-coated with silica (R) were measured like in Embodiment 1. A result of the measurement is shown in FIG. 4 to FIG. 6 and in Table 2.

TABLE 2

|  | Color difference (ΔE) | |
|---|---|---|
|  | CTG 16 wt % | Water 16 wt % |
| Non-coated red pigments (R): | 11 | 11 |
| Silica-coated red pigments (Rs): | 4.9 | 3.3 |
| Decrease rate (%) of ΔE: | 55 | 70 |

Like in a case of titanium oxide white pigments, change in a color tone of the red pigments coated with silica (Rs-c), (Rs-w) is smaller as compared to that of the red pigments non-coated with silica (R-c), (R-w) even when moistened with CTG and water.

Embodiment 3

Yellow iron oxide pigments coated with silica (Ys) was obtained by the same method as that described above excluding only the point that yellow iron oxide pigments (Y) made from needle-shaped particles each having an average length of 500 nm and an average diameter of 100 nm was used in place of the titanium oxide used in Embodiment 1. Observation of the yellow pigments with an electronic microscope showed that the particles had not be aggregated and particles shapes and diameters before and after coating with silica were substantially identical.

Figure 7:
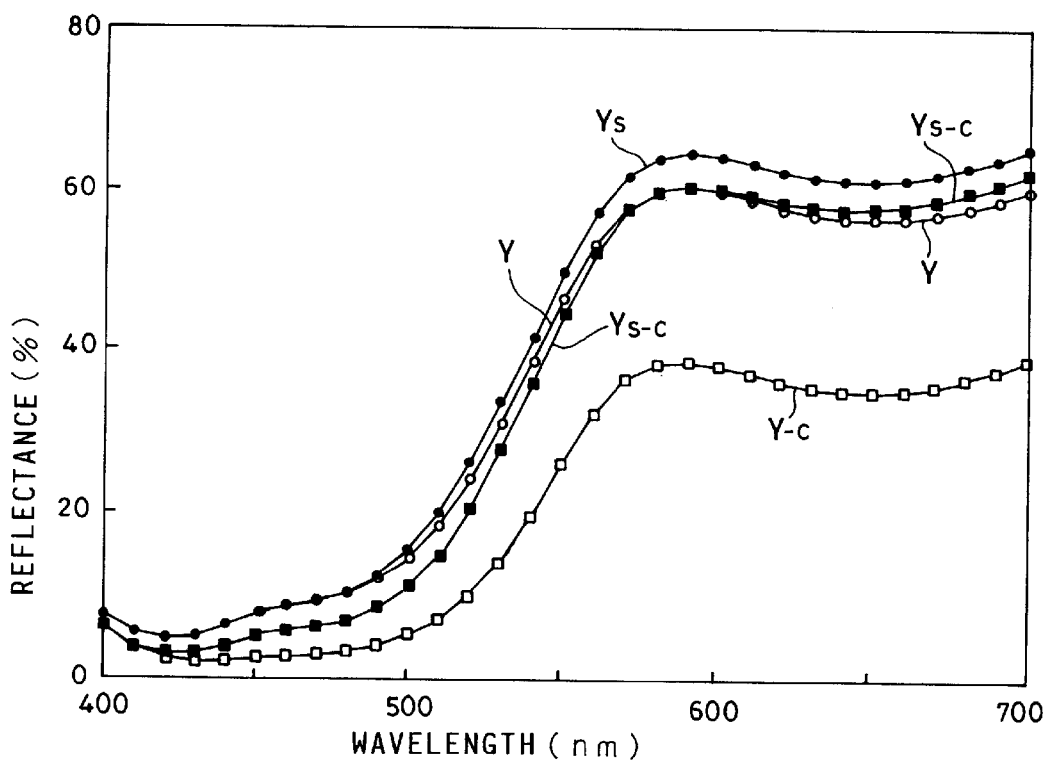
FIG. 7 is a graph showing a change in the reflectance when the yellow pigments (Y, Ys) are moistened with CTG.
Figure 8:
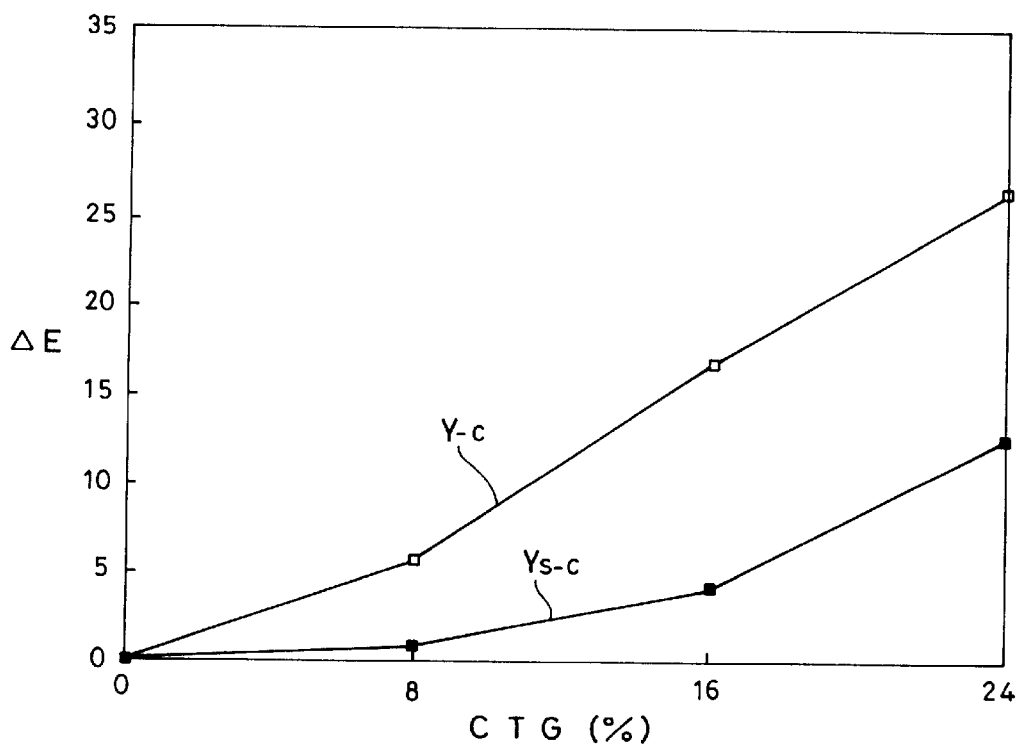
FIG. 8 is a graph showing a color difference of the yellow pigments (Y, Ys) when the pigments are moistened with CTG.
Figure 9:
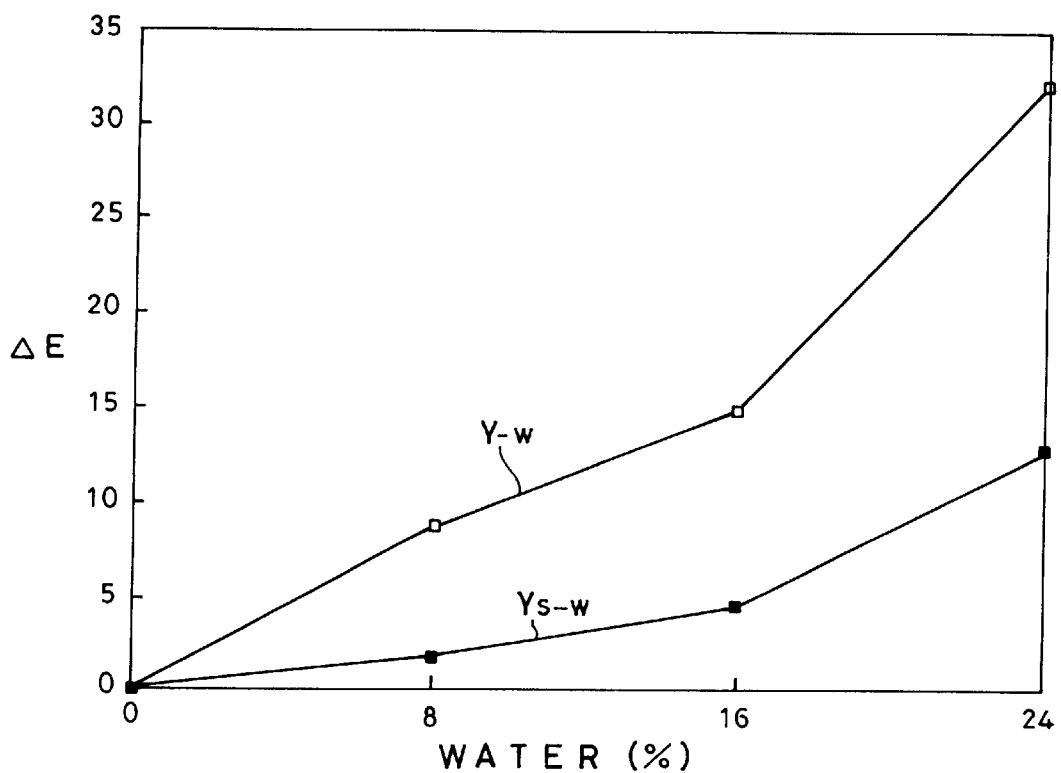
FIG. 9 is a graph showing a color difference of the yellow pigments (Y, Ys) when the yellow pigments are moistened with water.

Changes in a color tone of the resultant yellow pigments coated with silica (Ys) and yellow pigments non-coated with silica (Y) were measured like in Embodiment 1. A result of the measurement is shown in FIG. 7 to FIG. 9 and in Table 3.

TABLE 3

|  | Color difference (ΔE) | |
| --- | --- | --- |
|  | CTG 16 wt % | Water 16 wt % |
| Non-coated yellow pigments (Y): | 17 | 15 |
| Silica-coated yellow pigments (Ys): | 4.1 | 4.4 |
| Decrease rate (%) of ΔE: | 76 | 71 |

It is understood from the table above that, like in a case of the titanium oxide white pigments, change in a color tone of the yellow pigments coated with silica (Ys-c), (Ys-w) is smaller as compared to that of the yellow pigments non-coated with silica (Y-c), (Y-w) even when moistened with CTG or water.

Embodiment 4

The foundation containing the following ingredients was prepared:

|  | Weight % |
| --- | --- |
| (1) White pigments coated with silica (Ws) | 10.7 |
| (2) Red pigments coated with silica (Rs) | 0.55 |
| (3) Yellow pigments coated with silica (Ys) | 2.5 |
| (4) Black iron oxide | 0.15 |
| (5) Talc | 20 |
| (6) Synthesized mica | 36.9 |
| (7) Sericite | 17 |
| (8) Silica beads | 4.2 |
| (9) Silicone oil | 3 |
| (10) Squalane | 3.2 |
| (11) Ester oil | 1.6 |
| (12) Solbitane sesquiorate | 0.2 |
| (13) Perfume | As required |
| (14) Ethylparaben | As required |

At first, a mixture of the ingredients (1) to (8) was prepared. The ingredients (1) to (3) were pigments obtained in Embodiments 1 to 3. Then the ingredients (9) to (14) were fully mixed under a temperature of 70° C., and the mixture was added into the mixture of the ingredients (1) to (8), and the two mixtures were mixed to obtain a homogeneous mixture. The resultant mixture was dried, pulverized to particles each having a homogeneous size, and compressed for molding.

The resultant foundation was applied to faces of woman panelers, and the cosmetic effect in 3 hours was assessed. It was observed that the hiding performances became slightly lower in the so-called T zone comprising a brow and a bridge of a nose where sebum is much secreted, but that in other portions of the face the cosmetic effect immediately after application thereof was preserved as it was.

Comparative Embodiment 1

In Embodiment 4, a powder foundation was prepared by the same method excluding only the point that the white (W), red (R), and yellow (Y) pigments non-coated with silica used in Embodiment 1 to 3 above were blended in place of the white (Ws), red (Rs), and yellow (Ys) pigments coated with silica respectively. This foundation was assessed in the same way as that described above, and it was observed that the color tone was changed to a thin brown color on the entire face, especially in the T zone or an area close to a cheek with the hiding performances substantially lowered and that the excellent cosmetic effect could not be obtained.

Embodiment 5

90 g of the same titanium oxide white pigments (W) as that used in Embodiment 1 was suspended in water so that the concentration was 10 weight %, the suspension was heated to 80° C., then 10 wt % aluminium sulfate solution with the weight equivalent to 10 g of $Al_2O_3$ was added to the suspension over four hours while maintaining the pH at around 6 by adding a sodium hydroxide solution. The suspended particles were coated by alumina hydrate deposited on surfaces of the suspended particles.

Then the suspended particles were filtered, washed, and dried under a temperature of 110° C., and sintered under 600° C., and titanium oxide white pigments coated with alumina (Wa) were obtained. These white pigments were observed with an electronic microscope, and it was observed that the particles had not been aggregated and a form and a size of the particles had not changed from those before coating with alumina.

Change in a color tone of the resultant white pigments coated with alumina (Wa) when moistened with oil and water was measured and assessed like in Embodiment 1. Color differences (ΔE) when the mixing ratio of pigments vs CTG was 84/16 (weight ratio) and when the mixing ratio was 84/16 (weight ratio) are shown in Table 4, and the result was almost the same as that obtained for the white pigments coated with silica (Ws).

TABLE 4

|  | Color difference (ΔE) | |
| --- | --- | --- |
|  | CTG 16 wt % | Water 16 wt % |
| Non-coated white pigments (W): | 4.5 | 8.8 |
| Alumina-coated white pigments (Wa): | 1 | 1 |
| Decrease rate (%) of ΔE: | 78 | 89 |

Embodiment 6

Black iron oxide pigments coated with silica (Bs) were obtained by the same method excluding only the point that black iron oxide (B) made from needle-shaped particles each having an average length of 500 nm and an average diameter of 100 nm was used in place of the titanium oxide in Embodiment 1. This black pigments were observed with an electronic microscope, and it was found that a form and a size of the particles were substantially identical to those before coating with silica.

Then 10 g of the black iron oxide pigments coated with silica (Bs), 10 g of black iron oxide (B) and nothing were added in three vessels $V_1$, $V_2$ and $V_3$ each containing 100 g of soybean oil respectively. The samples were agitated under 98° C. and air was supplied into each vessel at a rate of 2.33 milli-liter/sec over six hours. Then the samples were cooled, the soybean oil with pigments added therein was filtered, and a peroxide value of each soybean oil sample was measured for assessing a degree of oxidation.

The peroxide value was measured by mixing soybean oil in a solvent prepared by mixing chloroform and acetic acid at a volume ratio of 2:3 and by iodometry. A result of the measurement is shown in Table 5, and it is understood from Table 5 that the black iron oxide pigments coated with silica (Bs) were substantially inert to soybean oil and had the capability of suppressing decomposition of the organic compounds such as oily components.

TABLE 5

| Vessel | Type of soybean oil | Peroxide value (milli-equivalent/kg) |
|---|---|---|
| — | Unprocessed soybean oil | 4.3 |
| $V_1$ | Bs added soybean oil | 19.6 |
| $V_2$ | B added soybean oil | 173.2 |
| $V_3$ | Nothing added soybean oil | 18.2 |

Embodiment 7

An experiment for generation of active oxygen was carried out for the pigments coated with an inorganic compound according to the present invention. Aging due to active oxygen can not directly be examined on human skin, so that the indirect method as described below was carried out. Namely, it is generally known that generation of acetone from isopropyl alcohol is performed through the oxidation reaction indicated by the following model equation (3):

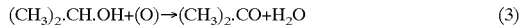

$$(CH_3)_2.CH.OH+(O) \rightarrow (CH_3)_2.CO+H_2O \qquad (3)$$

50 g isopropyl alcohol was put in each of two glass vessels $V_4$, $V_5$ with 10 g titanium oxide white pigments coated with silica (Ws) obtained in Embodiment 1 added in the vessel $V_4$ and 10 g titanium oxide white pigments (W) used in Embodiment 1 added in the vessel $V_5$, then air in each vessel was replaced with nitrogen gas, each vessel was shielded and exposed to sun light for one month. Then acetone in isopropyl alcohol with pigments having been removed therefrom was analyzed by means of the gas chromatography. Acetone was detected in isopropyl alcohol with titanium oxide white pigments (W) added therein, but was not detected in isopropyl alcohol with titanium oxide white pigments coated with silica (Ws) added therein.

Further generation of active oxygen was checked for titanium oxide white pigments coated with silica (Ws) and titanium oxide white pigments (W) respectively with an electronic spin resonance device (manufactured by Nippon Denshi: JES - TE200). 50 µg pigments, 200 µliter ultra-pure deionized water, and 30 µliter of spin trap agent (DMPO) were put in a glass test tube, supernatant was recovered in around 30 seconds and measured. Signals caused by active oxygen were observed in all samples, and it was observed that a peak due to active oxygen and a volume of generated active oxygen in the titanium oxide white pigments coated with silica (Ws) were smaller as compared to those in the titanium oxide white pigments(W).

We claim:

1. Pigments with surfaces coated homogeneously with an inorganic compound having refractive index of at most 1.8 and selected from the group consisting of alumina and phosphorus oxide, said pigments having an average diameter between 0.1 and 1 µm and being selected from a group consisting of, as inorganic pigments, titanium oxide, zinc oxide, ziconium oxide, cerium oxide, Indian red, yellow iron oxide, black iron oxide, ultramarine blue, dark blue, barium sulfate, titanated mica, mica, sericite, talc, bentonite, kaolin and mixed pigments with a color of human skin formed of titanium oxide and iron oxide, and as organic pigments, Red No. 202, Red No. 203, Red No. 204, Red No. 205, Red No. 207, Orange No. 203, Orange No. 204, Yellow No. 205, Blue No. 201 and Blue No. 204, said pigments having a decrease rate of a color difference defined by Hunter's color difference formula defined in 6.3.2 of JIS Z 8730 in a range from 55 to 84% when caprylic triglyceride is mixed at a (pigments)/(caprylic triglyceride) mixing ratio of 84/16 by weight so that a change of color of the pigments when caprylic triglyceride is added to the pigments is reduced.

2. Pigments according to claim 1, wherein said inorganic compound is coated onto the pigments in a range of 1–40 weight parts relative to 100 weight parts of the pigments.

3. Cosmetics containing the pigments according to claim 1.

4. Cosmetics according to claim 3, wherein said pigments are included in the cosmetics in a range of 1–80 wt %.

5. Pigments with surfaces coated honogeneously with an inorganic compound having refractive index of at most 1.8 and selected from the group consisting of alumina and phosphorus oxide, said pigments having an average diameter between 0.1 and 1 µm and being selected from a group consisting of, as inorganic pigments, titanium oxide, zinc oxide, zirconium oxide, cerium oxide, Indian red, yellow iron oxide, black iron oxide, ultramarine blue, dark blue, barium sulfate, titanated mica, mica, sericite, talc, bentonite, kaolin and mixed pigments with a color of human skin formed of titanium oxide and iron oxide, and as organic pigments, Red No. 202, Red No. 203, Red No. 204, Red No. 205, Red No. 207, Orange No. 203, Orange No. 204, Yellow No. 205, Blue No. 201 and Blue No. 204, said pigments having a decrease rate of a color difference defined by Hunter's color difference formula defined in 6.3.2 of JIS Z 8730 in a range of 70 to 89% when water is mixed at a (pigments)/(water) mixing ratio of 84/16 by weight so that a change of color of the pigments when water is added to the pigments is reduced.

6. Pigments according to claim 5, wherein said inorganic compound is coated onto the pigments in a range of 1–40 weight parts relative to 100 weight parts of the pigments.

7. Cosmetics containing the pigments according to claim 5.

8. Cosmetics according to claim 7, wherein said pigments are included in the cosmetics in a range of 1–80 wt %.

* * * * *